United States Patent [19]
Boone et al.

[11] Patent Number: 5,919,142
[45] Date of Patent: Jul. 6, 1999

[54] ELECTRICAL IMPEDANCE TOMOGRAPHY METHOD AND APPARATUS

[75] Inventors: Kevin Graham Boone; David Simon Holder, both of London, United Kingdom

[73] Assignee: BTG International Limited, London, United Kingdom

[21] Appl. No.: 08/994,757

[22] Filed: Dec. 19, 1997

Related U.S. Application Data

[63] Continuation of application No. PCT/GB96/01499, Jun. 21, 1996.

[30] Foreign Application Priority Data

Jun. 22, 1995 [GB] United Kingdom .................. 9512717

[51] Int. Cl.$^6$ ........................................................ A61B 5/05
[52] U.S. Cl. ................................................................ 600/547
[58] Field of Search ............................................. 600/547

[56] References Cited

U.S. PATENT DOCUMENTS

| | | | |
|---|---|---|---|
| 5,272,624 | 12/1993 | Gisser et al. ............................. | 600/547 |
| 5,465,730 | 11/1995 | Zadehkoochak et al. ............... | 600/547 |

FOREIGN PATENT DOCUMENTS

| | | |
|---|---|---|
| 43 01 483 | 8/1994 | Germany . |
| WO 88/07392 | 10/1988 | WIPO . |
| WO 91/19454 | 12/1991 | WIPO . |

OTHER PUBLICATIONS

D. S. Holder, "Electrical Impedance Tomography with Cortical or Scalp Electrodes During Global Cerebral Ischaemia in the Anaesthetised Rat", Clin. Phys. Physiol. Meas., 1992, vol. 13, No. 1, pp. 87–98.

R. Guardo et al., "A Superheterodyne Serial Data Acquisition System for Electrical Impedance Tomography", Proceedings of the Annual International Conference of the IEEE Engineering in Medicine and Biology Society, vol. 15, Oct. 1993, pp. 86–87.

K. Boone et al., "Imaging of Cortical Spreading Depression by EIT: Implications for Localization of Epileptic Foci", Physiol. Meas. 15, 1994, pp. A189–A198.

D. S. Holder, "Impedance Changes During the Compound Nerve Action Potential: Implications for Impedance Imaging of Neuronal Depolarisation in the Brain", Medical & Biological Engineering & Computer, No. 2, Mar. 1992, pp. 140–146.

D. C. Barber et al., "Applied Potential Tomography", J. Phys. E: Sci. Instrum., vol. 17, 1984, The Institute of Physics, pp. 723–733.

D. S. Holder, Impedance Changes During Evoked Nervous Activity in Human Subjects: Implications for the Application of Applied Potential Tomography (APT) to Imaging.

*Primary Examiner*—Ruth S. Smith
*Attorney, Agent, or Firm*—Pillsbury Madison & Sutro, LLP

[57] ABSTRACT

A method and apparatus for use in imaging a body uses electrical impedance tomography (EIT). A plurality of electrodes are provided in electrical contact with the body around the periphery of the body. A first electrical input signal is applied to at least one of the electrodes over a first time period, and a second electrical input signal, which is preferably in inverted form of the first, then applied to the at least one of the electrodes over a subsequent, second time period. The resulting electrical output signal is measured at one or more pairs of the remaining electrodes over the first and second time periods and the difference between the measured signal obtained during the first time period and that obtained during the second time period is calculated to provide a difference signal. The difference signal can stored and used for image reconstruction. The invention has particular application in imaging neurological function within the body, where the impedance changes associated with neuronal depolarizations are very small and the resulting electrical signals measured at the body periphery are even smaller. By use of this technique electrical signals corresponding to the dynamic components of impedance change can be reinforced whilst those corresponding to other unwanted components can be cancelled.

9 Claims, 4 Drawing Sheets

ELECTRICAL IMPEDANCE TOMOGRAPHY METHOD AND APPARATUS

This application is a Continuation of PCT/GB96/01499, filed Jun. 21, 1996.

FIELD OF THE INVENTION

The present invention relates to imaging, and more particularly to a method and apparatus for use in imaging a body by means of the technique of electrical impedance tomography (EIT), also termed "applied potential tomography" (APT). In particular, the invention may be used in imaging neurological function within the body.

BACKGROUND

Over the past few years there has been considerable interest in clinical applications of EIT, and such applications have extended to areas such as imaging changes in the thorax during breathing, in the stomach during gastric emptying and in the heart during intraventricular hemorrhage. EIT involves the application of spaced electrodes to the skin surface of a body under investigation, usually in the form of a belt around the body such that the electrodes lie in the plane of the body to be investigated. In a typical biomedical EIT system, low voltage alternating electrical current is applied between two neighboring electrodes (known as a drive pair) and the resulting potentials measured between pairs (known as driven pairs) of all the remaining electrodes. The potentials are recorded and the sequence repeated for all the other drive pairs, giving a matrix of measured impedance signal values. For example, the use of 16 electrodes provides a total of 104 independent impedance measurements. Using known reconstruction techniques this matrix can be processed by appropriate computer hardware to regenerate an image of impedance within the body plane. EIT methods and equipment have undergone considerable development and by making use of techniques such as parallel data collection and noise reduction, real time systems are now available capable of providing clinically useful images of dynamic phenomena. The basis of EIT is described in more detail in the paper "Applied Potential Tomography", Barber & Brown, 1984, J. Phys. E: Sci. Instrum., 17, 723–733. It is to be noted that neither the drive pair nor the receive pair need to comprise two adjacent electrodes, and in some cases a diametric drive pair and/or receive pair may offer certain advantages for clinical measurements.

One potentially interesting area for application of EIT techniques is in the clinical neurosciences, where scalp measurements are used to obtain images of functional changes in the human or animal brain. It is possible with existing equipment to form images of neural functional activity, such as that associated with stroke or spreading depression in a patient, due to the fact that cell swelling within the cortex of such subjects produces impedance increases of up to 30% ("Electrical impedance tomography with cortical or scalp electrodes during global cerebral ischaemia in the anaesthetised rat", D S Holder, Clin. Phys. Physiol. Meas. 1989, Vol. 13, No. 1, 87–98, and "Imaging of cortical spreading depression by EIT: Implications for localization of epileptic foci", K Boone, A M Lewis and D S Holder, Physiol. Meas. 15 (1994) A189–A198).

It has also been suggested that the much smaller changes in impedance during neuronal discharge might be measured by EIT techniques. ("Impedance changes during evoked nervous activity in human subjects: implications for the application of applied potential tomography (APT) to imaging neuronal discharge", D. S. Holder, Clin. Phys. Physiol. Meas. 1989, Vol. 10, No. 3, 267–274). The principle of this application is that the impedance of the neuronal membranes is known to fall during the action potential or during the sub-threshold depolarizations which accompany synaptic activity, and there may be other related effects such as the movement of ions between intra- and extra-cellular compartments. By use of scalp electrodes, changes in impedance taking place in the brain may be recorded and used to image the progress of information along circuits within the brain. For example, the brain may be stimulated by a visual signal and EIT images subsequently reconstructed for each millisecond or so of the recording window, thus enabling the resultant action potential processes to be tracked along their pathways in the subject's brain. There is no established technique which at present permits accurate imaging of neuronal depolarization with millisecond or sub-millisecond time resolution. MRI and PET techniques produce images of cerebral activity, but these are related to metabolic recovery processes, which occur over seconds or minutes.

One of the problems with this approach is that the impedance changes associated with action potentials are generally very small and very rapid. Even if there is a substantial decrease in the resistance of the neuronal membranes themselves when they depolarize, the impedance of the tissue as a whole may not change in the same proportion, because the amount of current that enters the neuronal axoplasm depends more on the absolute impedance of the nerve axons and their geometry than it does on the membrane impedance. One study has estimated that the changes in impedance are, at most, between 0.1 and 1% of the resting impedance, depending on the area of the brain concerned. It is therefore clear that the resolution and sensitivity of an EIT system will need to be very high to accurately image such small changes using measurements taken using scalp electrodes, and currently available devices are not capable of producing such images.

Investigations into the above-mentioned technique of imaging action potentials have been carried out using a prototype system employing square wave excitation of 50 $\mu$A at 5 Hz applied to a saline phantom. The square wave signal was chosen because the capacitive properties of the cell membranes mean that the high frequencies used in conventional EIT systems are generally unsuitable. The resulting inter-electrode potentials were sampled at a rate of 4000 frames per second and 100 sets of frames were averaged to produce the results. The results of the experiment showed a signal-to-noise ratio of 40–50 dB and reciprocity errors of 10%–20%. Images of discrete resistivity changes of less than 10% could be obtained but with significant systematic errors. The prototype was thus found to be unsuitable for neurophysiological imaging.

One of the problems of the prototype system has been that of noise. With the square wave signal used the amplifiers will detect a higher level of extraneous noise than would be the case with an AC system. 50 Hz mains interference lies within the recording bandwidth, as does intrinsic EEG activity associated with the action potentials. Previous systems have attempted to minimize the noise effects by filtering or averaging, but such attempts have met with limited success.

SUMMARY OF THE INVENTION

It is an object of the present invention to provide an improved system suitable for use in EIT. According to a first aspect of the invention, there is provided a method for use in imaging a body by means of the technique of EIT comprising the steps of providing a plurality of electrodes in electrical contact with the body around the periphery of the body, applying a first electrical input signal to at least one of the electrodes over a first time period, applying a second electrical input signal to the at least one of the electrodes over a subsequent, second time period, measuring the resulting electrical output signal at one or more of the remaining electrodes over the first and second time periods, and calculating the difference between the measured signal obtained during the first time period and that obtained during the second time period, to provide a difference signal.

Preferably, the second electrical input signal is an inverted form of the first electrical input signal, and conveniently the first and second electrical input signals may be unidirectional signals of equal and respectively opposite sign.

In a preferred form, the applications of the first electrical input signal and that of the second electrical input signal are continuously alternated, the first and second time periods being equal, and the electrical signal measurements are taken at regular intervals during each time period.

The measurement step of the invention is preferably carried out on a number of different pluralities of electrodes, and images representative of the body are generated using said difference signal.

The signal application step may be carried out in synchronization with the application of a separate stimulus signal to the body.

In optimizing the method of the invention, it has been determined that the first and second time periods are preferably each between 0.1 and 1.0 seconds.

According to a second aspect of the invention, there is provided apparatus for use in imaging a body by means of the technique of EIT comprising a plurality of electrodes adapted for electrical contact with the body around the periphery of the body, means for applying a first electrical input signal to at least one of the electrodes over a first time period, means for applying a second electrical input signal to the at least one of the electrodes over a second, subsequent time period, means for measuring the resulting electrical output signals at one or more of the remaining electrodes over the first and second time periods, and means for calculating the difference between the measured signal obtained during the first time period and that obtained during the second time period, to provide a difference signal.

The apparatus preferably includes means for providing an inverted form of the first electrical signal to produce the second electrical signal, which means may comprise a switching means controlling an electrical current generator, electrically isolated from the measuring means. Said means may comprise one or more optical isolators.

BRIEF DESCRIPTION OF THE DRAWINGS

The invention will now be described in more detail by way of example with reference to the accompanying figures, in which.

DETAILED DESCRIPTION OF THE PRESENTLY PREFERRED EXEMPLARY EMBODIMENTS

Figure 1:
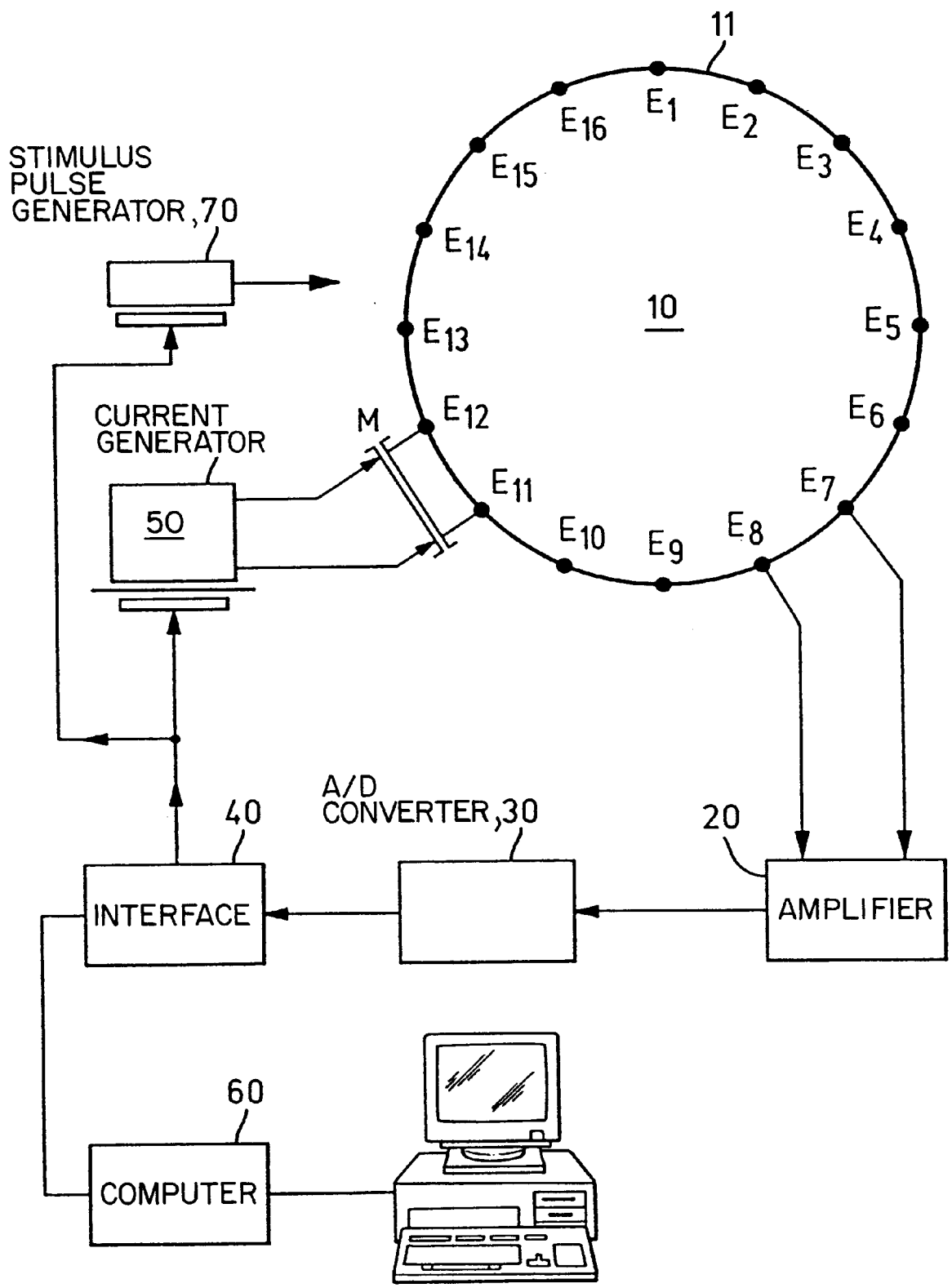
FIG. 1 shows in schematic form the main components of a 16 electrode EIT system as applied to neuronal imaging of a human subject.

Scalp electrodes $E_1$ to $E_{16}$ are shown in contact with the surface of subject's head 10 in FIG. 1. The electrodes are equally spaced and for this purpose may be provided on a flexible band 11 for selective positioning and attachment. Each electrode is connected by a lead to a switching means, such as a computer controlled current multiplexer M, whereby electrodes may be selected for application of a fixed current according to a desired excitation sequence. This general concept is well known in EIT techniques in general and will not be further described here. FIG. 1 shows an electrical signal from current generator 50 being applied between adjacent electrodes $E_{11}$ and $E_{12}$, whilst reference 70 represents a stimulus pulse generator (see below).

Signal measurements, in this case potential difference measurements, are made between others of the electrodes, and again methods of carrying out such measurements are generally known in the field of conventional EIT. It is noted that signal measurements made between different groups (e.g. pairs) of electrodes may be made sequentially or simultaneously (the latter technique known as parallel data collection). In the system illustrated in FIG. 1, signal measurement is carried out in parallel using 16 instrumentation amplifiers, each connected between an adjacent pair of electrodes. The figure illustrates only the measurement of the potential difference between electrodes $E_7$ and $E_8$ by way of amplifier 20.

The amplified measured electrical signals are then amplified and passed via signal processing means, such as a 16-bit analogue-to-digital converter 30 and a digital interface board 40, to be processed into an image by reconstruction software. Again, various reconstruction techniques and specific algorithms are known within the general field of EIT and will not be further described here. The resulting images represent tomographic images of the distribution of electrical characteristics across the cross section of the subject's brain in which the electrodes lie. The data acquisition control, image reconstruction, display and recording are all carried out by a microcomputer 60, which also provides a signal to drive a stimulus pulse device 70 (see below).

Figure 2:
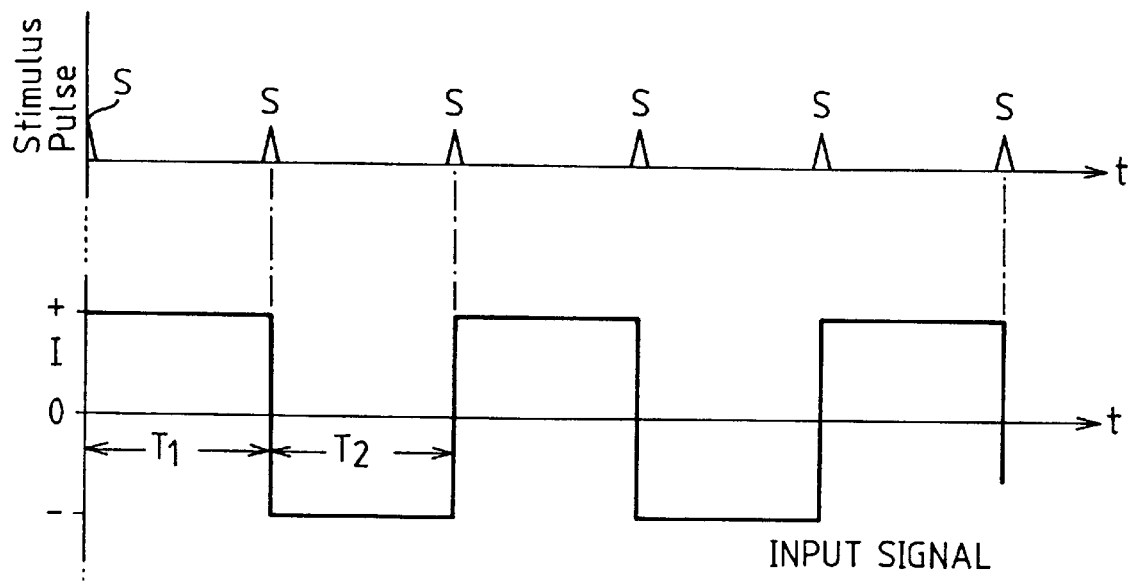
FIG. 2 illustrates an applied form of current excitation along with applied external stimulus pulses.

The lower trace of FIG. 2 illustrates the applied current excitation. As stated above, AC excitation is not well suited to investigating the activity of cells within the brain due to their capacitive character. According to the invention a bipolar waveform is selected, successively reversing the direction of constant current from a time period $T_1$ in which the signal is positive, to a time period $T_2$ in which the signals is of equal amplitude but of opposite, negative, polarity. An appropriate time for both periods $T_1$ and $T_2$ is 100 ms, and an appropriate current for neurophysiological application is 50 $\mu A$.

FIG. 2 also shows successive stimulus pulses S from generator 70, and in this case the pulses are coincident with the commencement of each period of the input current wave (upper trace). These stimulus pulses represent an external stimulation of the neurological function such as a flash of light (flash visual evoked response) or electrical stimulation of a nerve such as the median nerve at the wrist (sensory evoked response).

Figure 3:
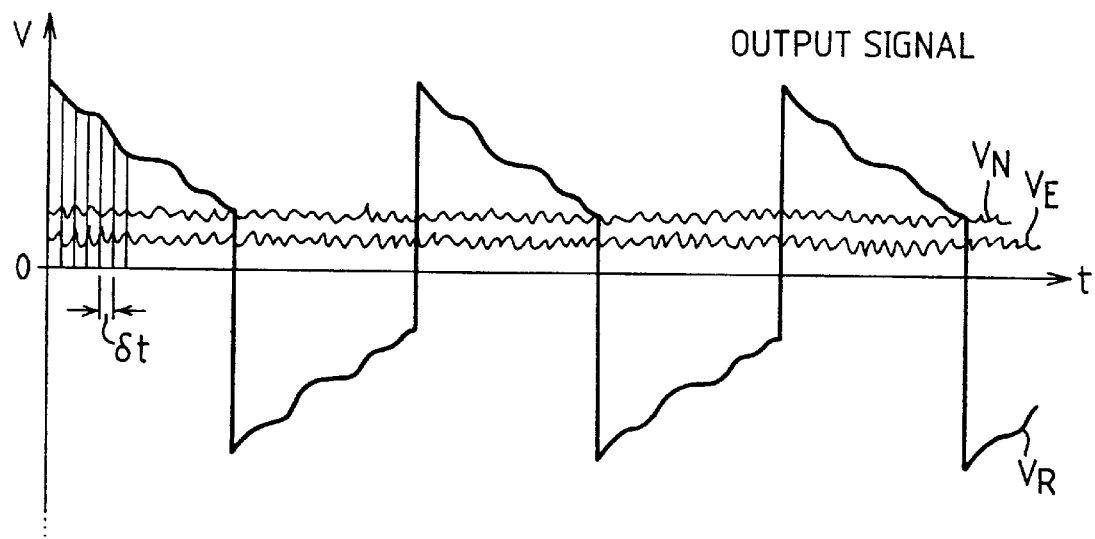
FIG. 3 schematically represents an example of measured potential difference (V) due to various sources, shown on a common axis.

As FIG. 3 illustrates, the signal is measured at a prescribed sampling rate with a time interval between samples of δt, representing preferably a large number of samples per time period of signal application. The signal measured can be seen as the sum of three components, namely that due to the dynamic impedance change taking place, $V_R$, that due to the patient's EEG signal, $V_E$, and that due to background noise such as the 50 Hz mains component, $V_N$. The $V_E$ component includes an electrical signal component evoked by the stimulus signals, i.e., due to the action potential itself. It will be appreciated that the figure is illustrative only and not to scale, being purely for purposes of explanation of the invention. As FIG. 3 shows, $V_R$ follows the polarity of the applied signal, whilst the other components are largely independent of the applied signal. The unwanted noise components $V_N$ and $V_E$ can be cancelled or at least significantly reduced by subtracting signals measured during time period $T_2$ from those measured at corresponding points during time period $T_1$. Components $V_R$ will reinforce, whilst those components independent of the bipolar input signal (i.e., $V_N$, $V_E$) will effectively cancel. The technique therefore makes use of all the measured data, the subsequent image reconstruction then being carried out using the signal representing the subtracted signals. Although the excitation polarity is reversed between each measurement time period, the biological response from a nerve (2–10 ms) is very much shorter than this, and the excitation can therefore be considered equivalent to DC.

In practice, to enhance the signal-to-noise ratio, the method is carried out by averaging measured signals over a succession of repeated stimulus pulses, the collected averaged data then being used for image reconstruction. Data are digitized and stored on the microcomputer 60.

Design and Calibration

The impedance measuring system described below was developed in respect of tests carried out firstly on a prepared crab nerve (in which resistivity changes are known to be up to 2.5%) using a tetrapolar arrangement and using an isolated constant voltage stimulator in electrical contact with the nerve as a synchronized stimulus, and secondly on the cerebral cortex of two anaesthetized rabbits, the resistance changes being evoked by a stimulus to the median nerve, again by way of an isolated constant voltage source.

For the crab nerve tests, the nerve was isolated in each case and suspended from the set of electrodes. The voltage stimulus was applied at one end of the nerve to generate an action potential, which propagated past the electrodes. For the rabbit cortex tests, a tetrapolar arrangement was again selected, transcranial electrodes applied over the most active part of the cortex. For both sets of test, an excitation current of about 10 μA was selected.

From these single channel measurements made on animal tissue the in-vivo measurements of the DC impedance showed clear changes during depolarization. In the case of the crab nerve, with an electrode spacing of 1 mm, the impedance measured along the length of the fibers was found to decrease during depolarization by 0.2–2.5% (mean value 1.0%). The resistance change measured perpendicular to the direction of the fibers was about 0.01%. In the case of the sensory cortex of the rabbit, these changes were found to be small but detectable, of the order of 0.01–0.03%.

Figure 4:
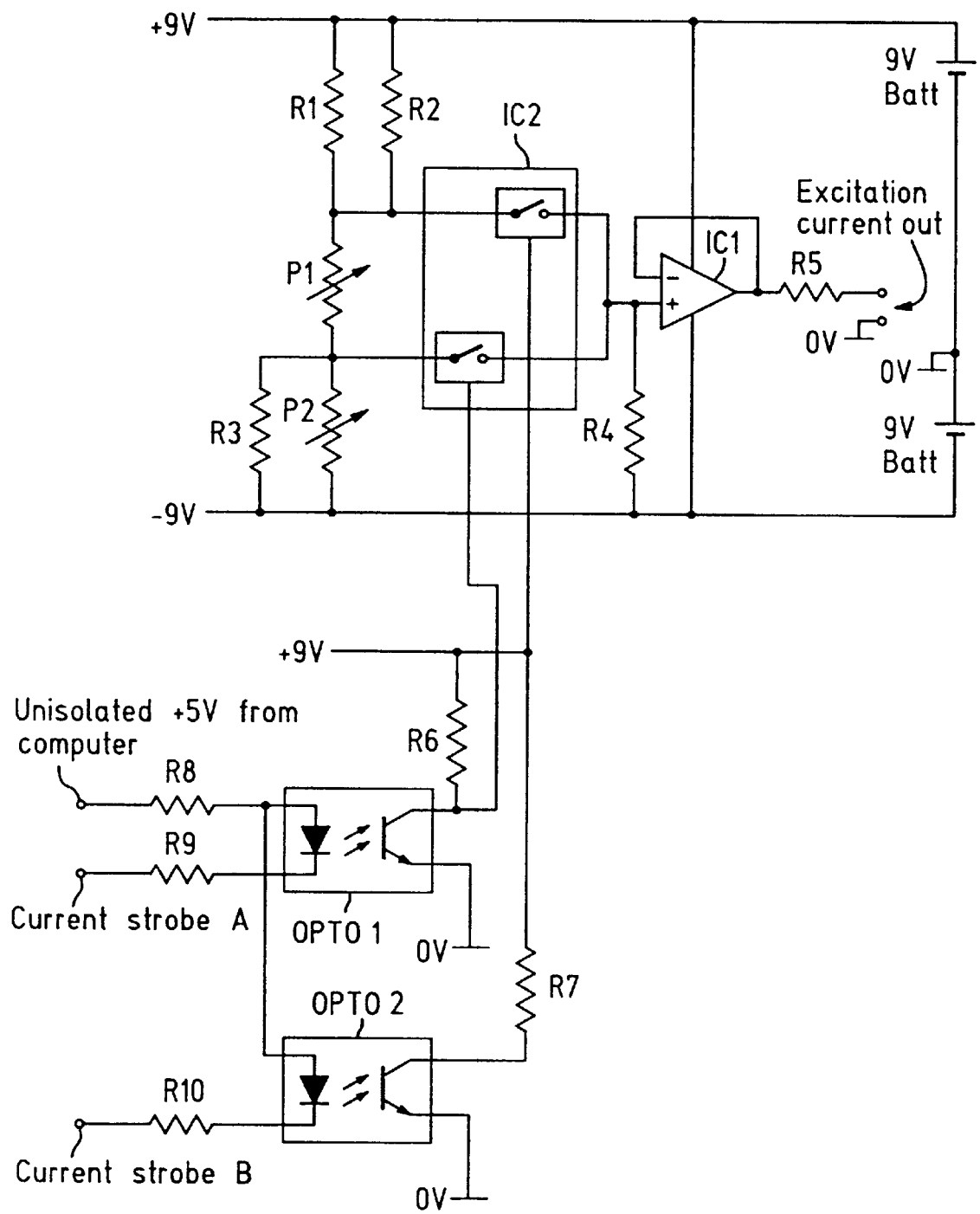
FIG. 4 is a circuit diagram of an isolated current generator.

The excitation protocol (that is, the reversal of polarity of excitation signal), has the advantage that as well as cancelling as far as possible unwanted signal components, it also serves to limit the extent of electrode polarization and to reduce any potential risk to the tissue under study. The impedance of the bare metal electrodes was found to be 2–10 kΩ even with this excitation protocol. To avoid the generation of common-mode voltages by the current source a current generator 50 (FIG. 1) electrically isolated from the recording system is used. The isolated current generator provides a current whose polarity is selected by the microcomputer 60 via a digital interface board 40 (see FIG. 1). A circuit diagram of the isolated current generator is shown in FIG. 4, and Table 1 gives values and specifications of the various components of the circuit.

Isolation is achieved by way of optical isolators OPTO1 and OPTO2 (Siemens SFH618-3-X001). Such a device consists essentially of an LED and a photo-transistor and provides a very high isolation voltage (>5000V). The computer selects the current polarity by switching using 'Current Strobe A' or 'Current Strobe B'. The term 'current strobe' is used herein to indicate a device producing a control signal which is able to cause selection of alternative conditions, in this instance, of alternative current configurations.

The constant current is achieved by connecting a constant voltage from the output of IC1 to the electrodes, via a large resistance R5 (500 kΩ). The size of the voltage is determined by switching equal and opposite control voltages from two 9V batteries connected in series onto the non-inverting terminal of IC1 using the analogue switches in IC2. The control voltages are derived from the resistor network consisting of resistances R1, R2 and R3 and trimmers P1 and P2. It is desirable to reduce as far as possible the stimulation of the nervous tissue under study by the current excitation itself. A current below the threshold for nerve stimulation is therefore preferably employed, and the circuit was designed such that adjustment of P1 sets the overall current level form 0–12 μA as follows. With P1 at its maximum value, the control voltage at the input of IC1 approaches the positive or negative supply voltage, depending on the settings of Current Strobes A and B. With P1 at its minimum value, the control voltage is close to zero.

TABLE 1

| Component | Value |
|---|---|
| R1, 3 | 1k |
| R2 | 27k |
| R4 | 120k |
| R5 | 500k |
| R6, 7 | 2k2 |
| R8, 9, 10 | 150R |
| P1 | 100k |
| P2 | 50k |
| IC1 | LF351 |
| IC2 | DG201 |
| OPTO1, 2 | SFH618-3-X001 |

For the control voltages to be equal and opposite, the resistances of parallel combinations R1|R2 and R3|P2 must be equal, as must the two battery voltages. In practice the batteries do not generate exactly equal voltages, and P2 was adjusted to balance the positive and negative output currents. Because the resistance of P2 is much higher than that of R3, P2 provides a very fine adjustment of the parallel resistance R3|P2. Re-balancing is necessary whenever either battery is replaced. It is to be noted that the ground points in the isolated current generator circuit refer to the junction of the two 9V batteries ('0V' in FIG. 4). It is important that this point remains internal to the generator, to avoid any current path between the generator and the computer or the differential amplifiers.

The differential amplifier 20 is of a known design using two different split supply rails set at voltages found to provide the best common-mode rejection. The gain is normally ×100, although ×10 and ×1000 were found to be occasionally useful in trials. Passive first-order filtering circuits were incorporated, serving to prevent any time-domain ripple that might manifest itself as a biological signal.

The data acquisition cycle is controlled by a computer programme, and in the tests a programm written in C++ for the Microsoft Windows environment on a Pentium(TM)-based PC was used. The maximum sampling rate possible was found to be 6000 samples per second, which was used for all measurements.

In practical application to EIT, the current multiplexer selecting electrodes for input signal application is controlled by the same program, allowing any combination of drive electrodes to be selected, and voltage measurement is carried out using 16 instrumentation amplifiers, each connected between an adjacent pair of electrodes around the body under investigation.

The program produced a record of comparison of the signals resulting from successive current applications of opposite polarity by subtracting the measurements of alternate cycles. The first two data acquisition cycles were as follows:

1. Set current strobe A high to switch on current generator; polarity positive (1)
2. Wait 20 ms for any transient effects to settle
3. Begin acquiring data (2) at 6000 samples per second, for 80 ms
4. Trigger the stimulus (3) one or more times during the period
5. Switch off current (4) by setting both current strobes set to low
6. Update impedance record
7. Set current strobe B high to switch on current generator; polarity reversed (5)
8–11. As 2–5 above
12. Subtract data from impedance record.

Figure 5:
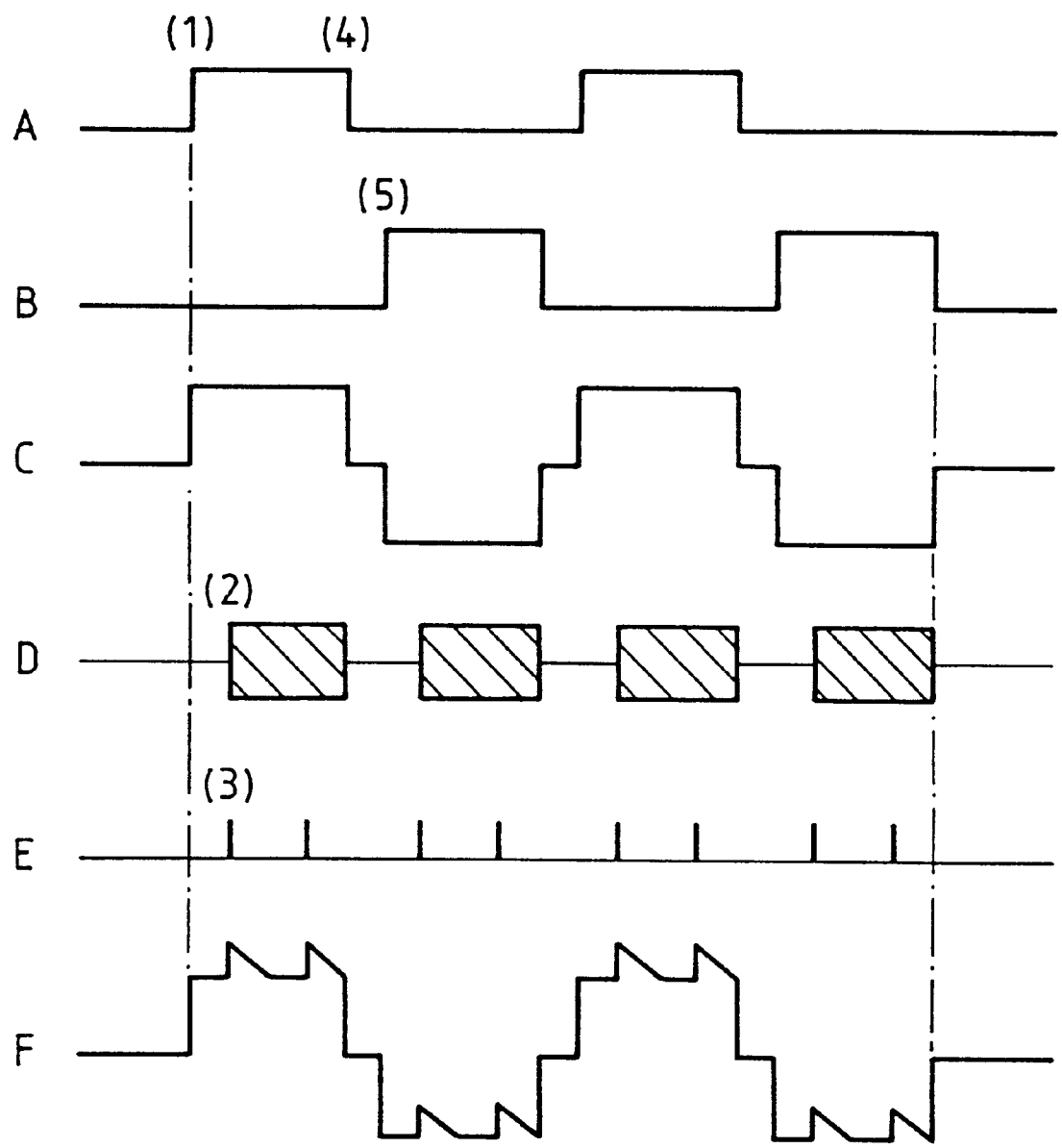
FIG. 5 illustrates a sequence of successive data acquisition cycles used in tests.

Subsequent pairs of cycles are identical, and a sequence of successive data acquisition cycles is illustrated schematically in FIG. 5. The traces shown are as follows:

A. Current strobe A
B. Current strobe B
C. Excitation current
D. Data collection periods
E. Stimulus to nerve
F. Voltage recording Points (1) to (5) in the described data acquisition cycles are shown in FIG. 5.

The above described system can be applied to producing images of activity in the brain with a temporal resolution of the order of the action potential (namely milliseconds) or less (down to a few microseconds). Ideally, such a technique would be used in humans with a ring of scalp electrodes. It also finds application in humans undergoing neurosurgery (e.g., for epilepsy) or in experimental animals if subdural or intracerebral electrodes are needed to provide adequate sensitivity. As the particular technique of the invention in applying interrogatory signals to a body may have advantages in reducing noise effects in EIT techniques in general, the invention may also find application in areas other than neurological investigation.

We claim:

1. A method for use in imaging a body by means of the technique of electrical impedance tomography (EIT), the method comprising:

provinding a plurality of electrodes in electrical contact with the body around the periphery of the body;

applying a stimulus to the body;

applying a first electrical input signal to at least one of the electrodes over a first time period;

applying a second electrical input signal to the at least one of the electrodes over a subsequent, second time period, wherein the second signal is an inverted form of the first electrical input signal;

measuring the resulting electrical output signal at one or more pairs of the remaining electrodes over the first and second time periods; and calculating the difference between the measured signal obtained during the first time period and that obtained during the second time period, to provide a difference signal.

2. A method according to claim 1, wherein the first and second electrical input signals are unidirectional signals of equal and respectively opposite sign.

3. A method according to any preceding claim, wherein the applications of the first electrical input signal and that of the second electrical input signal are continuously alternated, the first and second time periods being equal, and the electrical signal measurements are taken at regular intervals during each time period.

4. A method according to claim 1, wherein the measurement is carried out on a number of different pluralities of electrodes, and images representative of the body are generated using said difference signal.

5. A method according to claim 1, wherein the signal application is carried out in synchronization with the application of the stimulus signal to the body.

6. A method according to claim 1, wherein the first and second time periods are each between 0.1 and 1.0 seconds.

7. Apparatus for use in imaging a body suitable for use in the technique of electrical impedance tomography (EIT), the apparatus comprising:

a plurality of electrodes adapted for electrical contact with the body around the periphery of the body;

means for applying a first electrical input signal to at least one of the electrodes over a first time period;

means for applying a stimulus signal to the body;

means for providing an inverted form of the first electrical signal to produce the second electrical signal;

means for applying the second electrical input signal to the at least one of the electrodes over a second, subsequent time period;

means for measuring the resulting electrical output signals at one or more pairs of the remaining electrodes over the first and second time periods; and means for calculating the difference between the measured signal obtained during the first time period and that obtained during the second time period, to provide a difference signal.

8. Apparatus according to claim 7, further comprising:

an electrical current generator electrically isolated from the measuring means, and wherein the means for providing the inverted form of the first electrical input signal comprises a switching means controlling the electrical current generator.

9. Apparatus according to claim 8, wherein the electrical current generator is electrically isolated from the measuring means by one or more optical isolators.

* * * * *